United States Patent [19]

Pangburn

[11] Patent Number: 4,459,987
[45] Date of Patent: Jul. 17, 1984

[54] FLEXIBLE ABRASIVE PAD

[75] Inventor: William E. Pangburn, Ventura, Calif.

[73] Assignee: William W. Haefliger, Pasadena, Calif. ; a part interest

[21] Appl. No.: 356,830

[22] Filed: Mar. 10, 1982

[51] Int. Cl.³ .......................... A61B 17/00; B24B 3/46
[52] U.S. Cl. ..................................... 128/355; 51/401; 132/76.4
[58] Field of Search ................. 128/358; 51/400, 401, 51/402, 394–399, 403–407; 132/76.4

[56] References Cited

U.S. PATENT DOCUMENTS

| | | |
|---|---|---|
| 893,004 | 7/1908 | Miller . |
| 894,161 | 7/1908 | Miller . |
| 1,910,647 | 5/1933 | Steeg et al. . |
| 2,091,807 | 8/1937 | Crum . |
| 2,311,060 | 2/1943 | Lurrain . |
| 2,735,434 | 2/1956 | De Rossett . |
| 3,596,661 | 8/1971 | Metz . |
| 3,653,859 | 4/1972 | Zimmer ................................. 51/401 |
| 3,785,094 | 1/1974 | Holzhauer ............................ 51/401 |
| 3,910,284 | 10/1975 | Orentreich . |
| 4,034,769 | 7/1977 | Nishimura . |
| 4,184,499 | 1/1980 | Seidler . |

Primary Examiner—Stephen C. Pellegrino
Attorney, Agent, or Firm—William W. Haefliger

[57] ABSTRACT

A flexible cosmetic abrasive sheet comprises
 (a) a tough, flexible sheet of silicone polymer,
 (b) abrasive particulate carried by and protruding from at least one side of the sheet and exposed for rubbing contact with human skin during use of the sheet.

A layer of reticulated, resiliently compressible foam may be attached to the abrasive sheet, for light dermabrasion.

30 Claims, 15 Drawing Figures

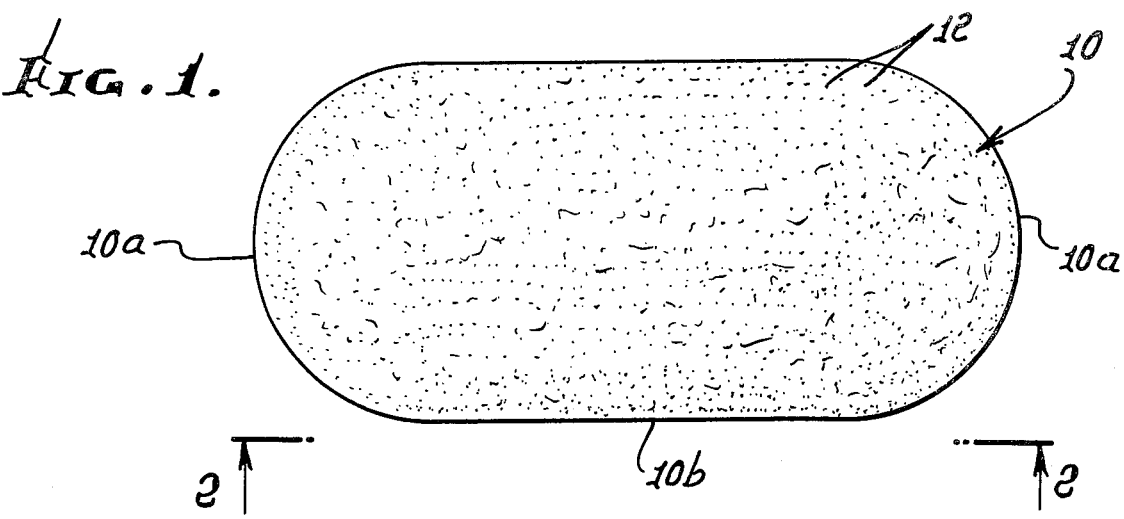
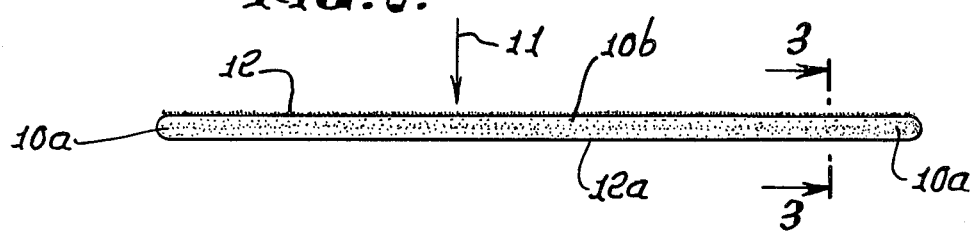
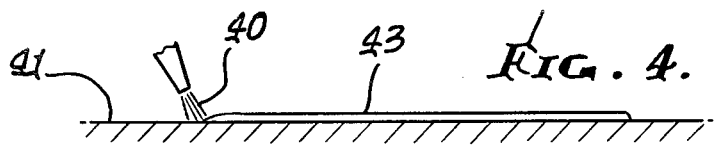
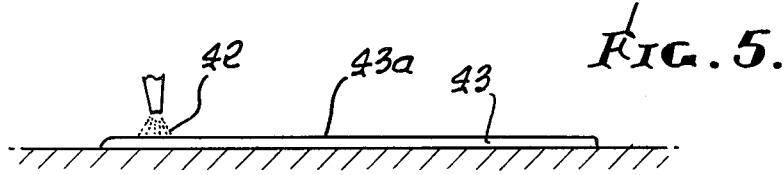
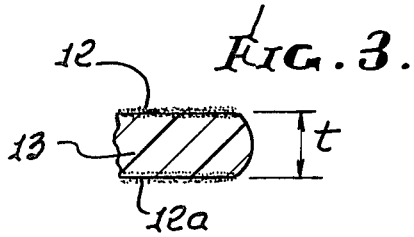
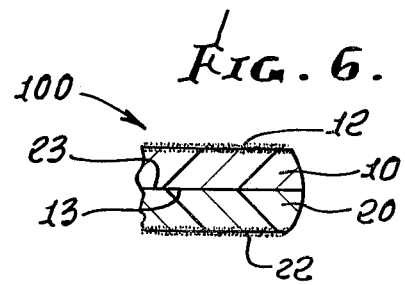
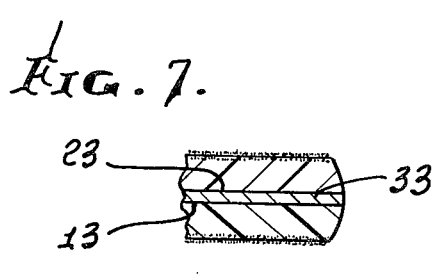
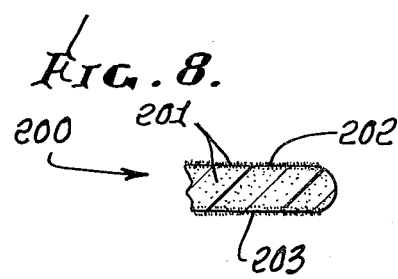

FLEXIBLE ABRASIVE PAD

BACKGROUND OF THE INVENTION

This invention relates generally to cosmetic abrasive devices, and more particularly concerns a tough, flexible and stretchable abrasive sheet that may be die cut or formed to many configurations useful in abrading skin surfaces as during callous removal, dermabrasive and other skin removal techniques.

At the present time, rigid abrading stones and unstretchable devices are manipulated to effect skin removal. Such rigid or unstretchable devices do not desirably conform to complexly curved skin contours, as for example at heels, elbows, etc. and consequently they are difficult to manipulate accurately to remove skin at selected areas only. As a result, skin "burns" can and do occur, and excess time is consumed in achieving selected skin area removal. There is need for a means which will obviate these difficulties.

SUMMARY OF THE INVENTION

It is a major object of the invention to provide a stretchable, variable shape material offering a solution to the above difficulties. Basically, the stretchable cosmetic abrasive sheet of the invention comprises a tough, shaped, flexible sheet of silicone rubber and abrasive particulate, compounded so that at least one side of the sheet will have particulate exposed edges for rubbing contact with human skin during use. As will be seen, this sheet is preferably stretchable and compressible to enhance its compatability to skin contours such as heels and elbows; further, the particulate preferably comprises pumice particles or the like. Also, the sheet thickness is between 0.015 and 0.100 inches. Further, two such sheets may be bonded together to provide a composite sheet, as will be seen.

The method of making the described sheet comprises the steps:

(a) forming a layer of incompletely cured silicone rubber, (b) combining abrasive particulate such as pumice with the rubber to adhere thereto, and (c) allowing the layer to cure to form a sheet with the particulate exposed at one side thereof for ultimate rubbing contact with human skin during use.

As will appear, the silicone-pumice initially contains a curing agent which disperses as the sheet cures. These and other objects and advantages of the invention as well as the details of an illustrative embodiment, will be more fully understood from the following description and drawings, in which:

DRAWING DESCRIPTION

FIG. 1 is a plan view of a die cut or formed sheet or pad embodying the invention;

FIG. 2 is an edge view taken on lines 2—2 of FIG. 1;

FIG. 3 is an enlarged fragmentary section taken on lines 3—3 of FIG. 2;

FIG. 4 is an elevation showing one step in formation of the FIG. 1 sheet or pad;

FIG. 5 is a view like FIG. 4 showing another step in formation of the sheet or pad; and FIGS. 6, 7 and 8 are views like FIG. 3 showing modified sheet or pad constructions;

DETAILED DESCRIPTION

Figure 9:
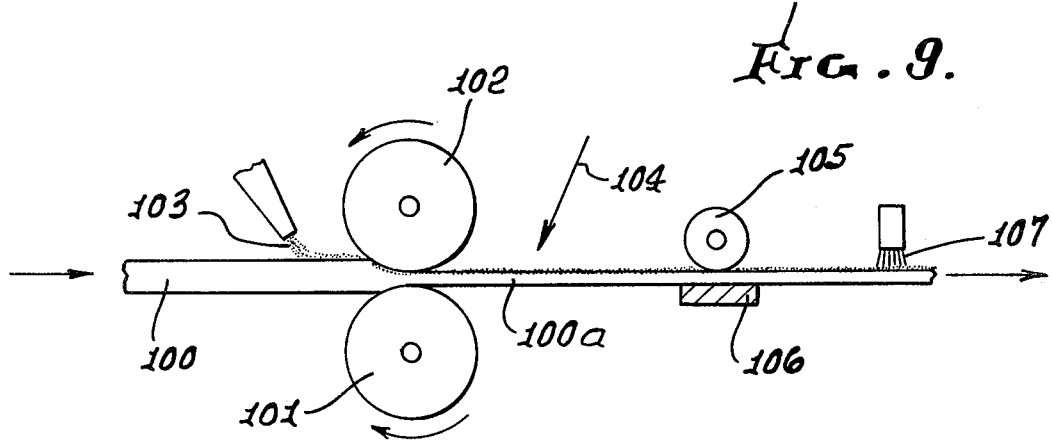
FIG. 9 is a side view showing a modified method of forming the silicone layer.

In FIGS. 1–3, a flexible, flat abrasive sheet is shown at 10, it also being somewhat stretchable to conform to contours of the body such as heels, elbows, etc. The sheet is also resiliently compressible in the direction 11, normal to the plane it defines. The sheet may preferably be die cut to shape, as for example lengthwise elongated, with rounded ends as at 10a.

The sheet preferably consists of pourable silicone polymer or adhesive sealant as for example General Electric RTV 108 which vulcanizes at room temperature. It contains a suitable curing agent. Also usable is GE RTV 118 which is self leveling when poured on a surface. RTV 108 and 118 are both translucent, tough and durable. The sheet is loaded with, or carries, abrasive particulate such as pumice or other fine abrasive suitable to abrading thickened areas of the skin. As shown, the protruding particulate 12 is located at at least one side of the sheet, and exposed for rubbing contact with the skin. FIG. 3 shows another like layer 12a at the opposite side of the sheet. The central layer 13 of silicone carries the particulate layers which are bonded to the silicone during curing, edges of particles penetrating the silicone mass. Note that particulate also covers the sheet or pad peripheral edges, as at 10b and 10a in FIG. 2, but this may be omitted.

Typically, the sheet thickness "t" is between 0.015 and 0.100 inches, and preferably between 0.020 and 0.060 inches.

In FIG. 6, the sheet or pad 100 includes a first sheet 10 having particulate 12 on one side, and a second sheet 20 having particulate 22 on one side. The two sheets have their opposite sides 13 and 23 bonded together as during curing so that the particulate layers 12 and 22 are exposed at opposite sides of the pad. In FIG. 7 the construction is the same, excepting for a separate bonding layer 33 attached to sides 13 and 23. Layer 33 may consist of polyester matte or other stretchable flexible fiber. FIG. 8 shows a modified sheet or pad 200 impregnated with particulate 201, so that edges of the particulate are exposed at the opposite sides of the sheet, 202 and 203 indicating such edges.

The method of making the pad is shown in FIGS. 4 and 5. In FIG. 4 the silicone polymer, is poured or spread at 40 on a flat surface 41. That surface advantageously consists of polyethylene at room temperature, so that the silicone will not adhere to same. Pumice particles are than dispensed as at 42 to cover the upper side 43a of the silicone layer 43 prior to complete curing. The particles become bonded to the silicone, and as the latter cures, the acetoxy or other curing agent vaporizes. The resultant sheet or pad has generally uniform thickness, and may be cut to shape. After about 15 to 20 minutes from time of pour at 40, the silicone layer or sheet is cured, at room temperature.

One usable silicone formulation is known as dimethyl polysiloxane, and the curing agent is acetic anhydride.

Another feature of the invention is to embody a finer grade of particle fineness at layer 12, and a coarser grade of particle fineness at layer 12a, as in FIG. 3.

Representative finenesses are as follows:

Fineness "A" (passes Tyler screen of mesh size 60, but will not pass screen mesh 80).

Fineness "B" (passes Tyler screen of mesh size 120, but will not pass screen mesh 140).

In FIG. 9, the sheet 100 (corresponding to sheet 10), prior to complete curing, is reduced in thickness, as by passage between calender rolls 101 and 102, thereby to form the final sheet 100a. Pumice such as particulate may be dispensed at 103 onto the upper surface of the sheet prior to passage of the sheet between the rolls, in which event the pumice is pressed into the sheet as by the roll 102. Alternatively, the pumice may be dispensed at 104 onto the sheet after it emerges from between the rolls 101 and 102. A presser unit, such as roller 105, may then be used to press the pumice into the sheet 100a as it slides over a backer 106, prior to completion of cure. A brush or compressed air stream, at 107, removes excess pumice from the sheet.

Figure 10:
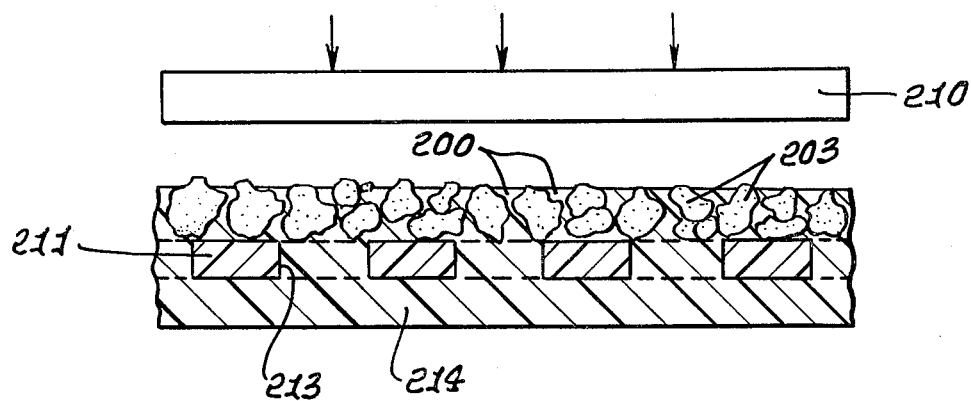
FIG. 10 is an enlarged side elevation showing a method of pressing particulate into the silicone layer.
Figure 10A:
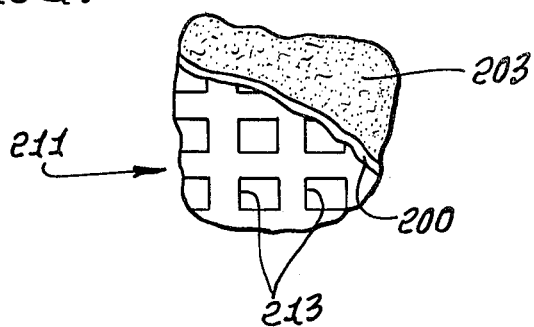
FIG. 10a shows a matte on which the silicone layer may be formed.

In FIGS. 10 and 10a the pumice particles 203 are shown as having been pressed, as by bar 210, into the silicone layer 200, so that the particle edges protrude from the layer 200. A matte sheet 211 in layer or sheet 200 supports the pumice, as shown. The matte contains mesh openings 213 into which the silicone layer extends, i.e. matte 211 is embedded in layer 200 and offers additional support to same. The matte may consist of polyester, NYLON, etc; it is stretchable (to stretch with layer 200); and it typically has a loose weave or configuration.

If desired, the FIG. 10 sheet can be inverted, and pumice particles pressed into area 214, in the same manner as particles 203 extend in layer 200.

Figure 11:
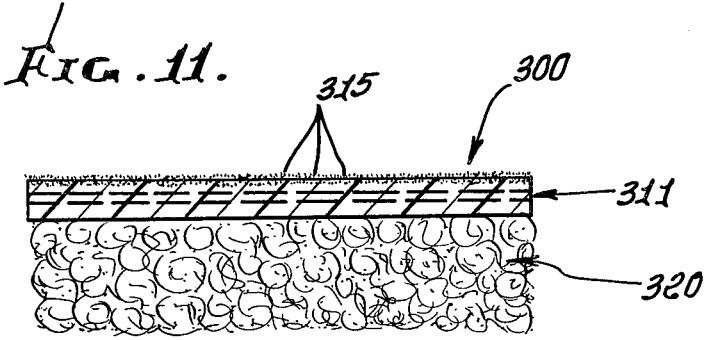
FIGS. 11–14 are elevations showing modifications.

In FIG. 11, the flexible first sheet is like that shown at 200 in FIG. 10, with a matte 311 embedded in the silicone polymer layer 300. Particulate (pumice for example) particles 315 are carried by the layer 300, as in FIG. 10, with edges exposed at a first side for relatively heavy duty dermabrasion (elbows, feet, etc.). A second sheet or layer 320 of reticulated foam that is resiliently compressible is attached to the sheet or layer 300, and projects at the second side thereof, as shown. The attachment may be effected by contacting one side of layer 320 with the uncured or partially cured layer 300, and allowing the cure to proceed to completion. Examples of the open work, fibrous sheet 320 are:

No. 3 Scott Industrial Foam, a reticulated polyester urethane product of Wilshire Foam Products Inc. Carson, Calif.

No. 4 Scott Safety Foam, reticulated urethane ester product of Wilshire Foam Products, Inc.

Such foam is useful for lighter dermabrasion and cleaning as well as massaging of more sensative skin areas, as face and neck. Thus, one device, as in FIG. 11, may have multiple functions, and the functional layers assist in supporting one another. Also, the openwork layer 320 is easily cleaned or freed of removed skin particles and soils, as by washing.

Figure 12:
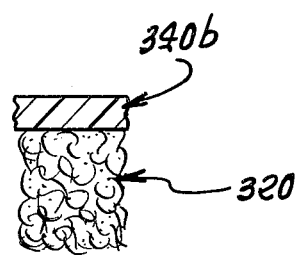
Figure 13:
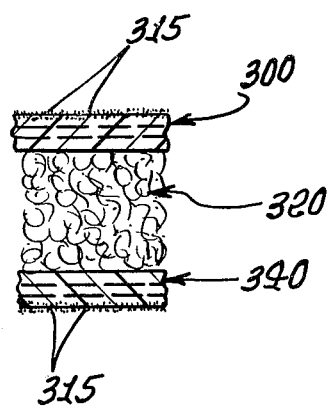
Figure 14:
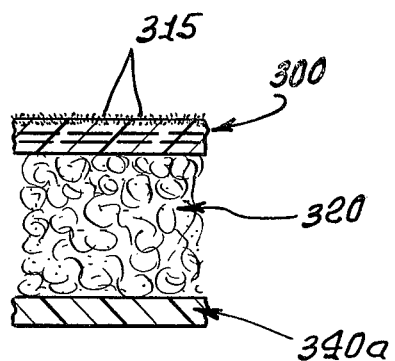

The device of FIG. 13 is like that of FIG. 12, and a third layer 340 is attached to the opposite side of the second layer 320. Third layer 340 is like layer 300, whereby the dermabrasion layers are interconnected by compressible layer 320. FIG. 14 is like FIG. 13, excepting that layer 340a contains no particulate. FIG. 12 is like FIG. 14, excepting that no layer 300 is used, layer 340b contains no particulate, and may consist of flexible, tough material.

Layer 320 is characterized as remaining distended after use; it does not "yellow" or discolor; and it has excellent wet abrading capability.

The thickness of layers 300, 340 and 340a are exaggerated in FIGS. 11-14.

I claim:

1. A flexible cosmetic abrasive sheet comprising
   (a) a tough, flexible sheet of silicone polymer,
   (b) abrasive particulate carried by and protruding from at least one side of the sheet and exposed for rubbing contact with human skin or other work during use of the sheet,
   (c) said sheet being stretchable, and being formed from a layer of initially incompletely cured silicone polymer with which said particulate has been combined to adhere to the sheet, the sheet then allowed to cure.

2. The sheet of claim 1 which has pad configuration.

3. The sheet of claim 2 which includes a second sheet as defined in (a) of claim 1 and abrasive particulate carried by and protruding from at least one side of the second sheet, the two sheets being bonded together so that the abrasive is exposed at opposite sides of the pad.

4. The pad of claim 3 wherein said abrasive particulate consists of pumice.

5. The sheet of claim 3 wherein said two sheets are spaced apart, and including a bonding layer sandwiched between said sheets.

6. The sheet of claim 5 wherein said bonding layer consists of a matte.

7. The sheet of claim 1 wherein said abrasive particulate consists of pumice or the like.

8. The sheet of claim 1 wherein abrasive particulate is also carried by and protrudes from the opposite side of the sheet and is exposed at said opposite side.

9. The sheet of one of claims 8 and 3 wherein the particulate at one side of the sheet has a first fineness, and the particulate at the opposite side of the sheet has a second fineness, said first and second finenesses being different.

10. The sheet of claim 1 wherein the sheet thickness is between 0.015 and 0.100 inches.

11. The sheet of claim 10 wherein the sheet thickness is approximately uniform over the sheet area, and is between 0.020 and 0.060 inches.

12. The sheet of one of claims 1-8 including a stretchable and flexible matte on which said layer is formed.

13. The method of forming flexible cosmetic abrasive sheet, that includes
    (a) forming a layer of incompletely cured silicone polymer,
    (b) combining abrasive particulate with said layer to adhere thereto, and
    (c) allowing said layer to cure to form a sheet with said particulate exposed at one side thereof for intimate rubbing contact with human skin during use.

14. The method of claim 13 wherein said layer is initially in liquid state and contains a curing agent, and said (c) step includes allowing the liquid to polymerize.

15. The method of claim 14 wherein said (a) step includes pouring said liquid onto a polyethylene surface at room temperature.

16. The method claim 13 including forming a second sheet as defined in claim 13 and bonding said two sheets to form a composite sheet.

17. The method of claim 13 wherein said (b) step is carried out by applying the particulate to the surface of said layer prior to completed curing thereof.

18. The method of claim 13 wherein said layer is formed to have a thickness between 0.020 and 0.060 inches after curing.

19. The method of claim 13 which further includes, prior to said (c) step, reducing the thickness of said layer.

20. The method of claim 19 wherein said reduction in thickness is effected by passing said layer between calender rolls.

21. The method of claim 20 including removing excess particulate from the sheet after it is passed between said rolls.

22. The method of one of claims 13 and 20 wherein said (b) step includes pressing the particulate into said layer, the particulate consisting essentially of pumice.

23. The method of one of claims 13, 19 and 22, that includes forming said layer on a flexible matte.

24. The method of one of claims 13, 19 and 22 that includes forming said layer on a flexible and stretchable matte, and pressing the particulate into the layer and toward the matte.

25. A composite cosmetic device, comprising
   (a) a tough, flexible first sheet of silicone polymer, and having first and second sides,
   (b) abrasive particulate carried by and protruding from the first side of the sheet and exposed for rubbing contact with human skin or other work, said sheet being stretchable, and being formed from a layer of initially incompletely cured silicone polymer with which said particulate has been combined to adhere to the sheet, the sheet then allowed to cure, and
   (c) a second sheet of resiliently compressible, reticulated foam attached to said silicone polymer sheet and projecting from said second side thereof.

26. The device of claim 25 wherein said foam consists essentially of polyurethane and has exposed fibrous edges.

27. The device of claim 25 wherein the foam is fibrous throughout, and has at least about 90% void space.

28. The device of claim 25 wherein said particulate consists of pumice or the like.

29. The device of claim 25 including a third sheet, the second sheet having opposite sides one of which is attached to said first sheet, and the other of which is attached to the third sheet.

30. The device of claim 29 wherein the third sheet consists essentially of silicone polymer, and abrasive particulate carried by the third sheet and exposed at the side thereof opposite said second sheet.

* * * * *